United States Patent
Wu et al.

(10) Patent No.: US 12,208,152 B2
(45) Date of Patent: Jan. 28, 2025

(54) ORAL CARE COMPOSITIONS CONTAINING SODIUM LAUROYL SARCOSINATE AND BETAINE

(71) Applicant: Colgate-Palmolive Company, New York, NY (US)

(72) Inventors: Shuyun Wu, Guangzhou (CN); Shaopeng Xu, Guangzhou (CN); Yunran Huang, Guangzhou (CN)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 17/383,934

(22) Filed: Jul. 23, 2021

(65) Prior Publication Data
US 2022/0023180 A1    Jan. 27, 2022

(30) Foreign Application Priority Data

Jul. 24, 2020    (CN) .......................... 202010727693.X

(51) Int. Cl.

| | | |
|---|---|---|
| *A61K 8/44* | (2006.01) | |
| *A61K 8/04* | (2006.01) | |
| *A61K 8/21* | (2006.01) | |
| *A61K 8/27* | (2006.01) | |
| *A61K 8/36* | (2006.01) | |
| *A61K 8/42* | (2006.01) | |
| *A61Q 11/00* | (2006.01) | |

(52) U.S. Cl.
CPC .............. *A61K 8/44* (2013.01); *A61K 8/042* (2013.01); *A61K 8/21* (2013.01); *A61K 8/27* (2013.01); *A61K 8/361* (2013.01); *A61K 8/42* (2013.01); *A61Q 11/00* (2013.01); *A61K 2800/30* (2013.01); *A61K 2800/596* (2013.01)

(58) Field of Classification Search
CPC .. A61Q 11/00; A61K 2800/596; A61K 8/042; A61K 8/21; A61K 8/27; A61K 8/361; A61K 8/42; A61K 8/44; A61K 8/442
See application file for complete search history.

(56) References Cited

U.S. PATENT DOCUMENTS

| | | | |
|---|---|---|---|
| 5,320,830 A | 6/1994 | Lukacovic et al. | |
| 8,906,348 B2 | 12/2014 | Narasimhan et al. | |
| 2010/0316580 A1 | 12/2010 | Kohli et al. | |
| 2012/0219606 A1* | 8/2012 | Deckner | A61K 8/25 424/53 |
| 2013/0315845 A1* | 11/2013 | Vogt | A61K 8/442 424/52 |
| 2015/0164778 A1* | 6/2015 | Obias | A61K 8/361 424/52 |

FOREIGN PATENT DOCUMENTS

| | | | |
|---|---|---|---|
| CN | 101938983 | 1/2011 | |
| CN | 104095771 A * | 10/2014 | |
| CN | 104666185 | 6/2015 | |
| CN | 107648062 | 2/2018 | |
| CN | 107648062 A * | 2/2018 | ............ A61K 8/345 |
| CN | 107982185 | 5/2018 | |
| CN | 107982185 A * | 5/2018 | |
| CN | 108888546 | 11/2018 | |
| CN | 109010090 | 12/2018 | |
| CN | 109010090 A * | 12/2018 | |
| CN | 109044898 | 12/2018 | |
| CN | 109044899 | 12/2018 | |
| CN | 109908025 | 6/2019 | |
| CN | 109953919 | 7/2019 | |
| WO | WO-9506455 A1 * | 3/1995 | .............. A61K 8/19 |
| WO | 1995/031175 | 11/1995 | |
| WO | WO-2012021415 A2 * | 2/2012 | .......... A61K 31/435 |

OTHER PUBLICATIONS

Google Patents English version of CN 104095771A, Fang et al. 2014 (Year: 2014).*
CN-109010090-A machine translation by Google Patents (Year: 2018).*
CN-107648062-A machine translation by Google Patents (Year: 2018).*
CN-107982185-A machine translation by Google Patents (Year: 2018).*
Anonymous, 2010, "Siberry Strengthening Toothpaste", Mintel Database GNPD AN: 1330949.
Anonymous, 2017, "Flouride Protector Toothpaste with Tea Tree Oil", Mintel Database GNPD AN: 4844385.
Anonymous, 2017, "Mint Anti-Cavity Toothpaste", Mintel Database GNPD AN: 5176037.
International Search Report and the Written Opinion of the International Searching Authority issued in International Application PCT/US2021/042932 mailed Nov. 15, 2021.

* cited by examiner

*Primary Examiner* — Walter E Webb
*Assistant Examiner* — Amanda Michelle Petritsch

(57) ABSTRACT

This invention relates to sodium lauryl sulfate (SLS)-free oral care compositions with improved foaming properties which comprise sodium lauroyl sarcosinate and a betaine, wherein the weight ratio of sodium lauroyl sarcosinate to the betaine is from 1:1.1 to 1:3.5, as well as to methods of using these compositions.

7 Claims, No Drawings

ORAL CARE COMPOSITIONS CONTAINING SODIUM LAUROYL SARCOSINATE AND BETAINE

CROSS REFERENCE TO RELATED APPLICATION

The present application claims the benefit of and priority under 35 U.S.C. § 119 to Chinese Application No. 202010727693.X, filed Jul. 24, 2020.

BACKGROUND

Conventional oral care products primarily utilize sodium lauryl sulfate (SLS) as surfactant to achieve good foam performance. However, some experimental studies indicate that SLS may cause epithelial desquamation and disrupt barrier function of oral mucosa. It may also exacerbate conditions that compromise epithelial integrity, e.g., apthtous ulceration. Therefore, it is important to find a replacement of SLS, especially for some sensitive consumers such as mouth sores sufferers, kids and pregnant women. There exists a need for surfactant systems having excellent foam performance which can be used to replace SLS in oral care compositions.

BRIEF SUMMARY

In one aspect, the invention provides an oral care composition, e.g., toothpaste or gel, comprising sodium lauroyl sarcosinate and a betaine, wherein the weight ratio of sodium lauroyl sarcosinate to the betaine is from 1:1.1 to 1:3.5. In some embodiments, the composition is free of sodium lauryl sulfate (SLS). In some embodiments, the betaine is cocamidopropyl betaine.

In some embodiments, sodium lauroyl sarcosinate is present in an amount of from 0.5% to 1% by weight of the composition and the betaine is present in an amount of from 1% to 1.5% by weight of the composition. In some embodiments, sodium lauroyl sarcosinate is present in an amount of from 0.5% to 0.9% by weight of the composition and the betaine is present in an amount of from 1.1% to 1.5% by weight of the composition. In some embodiments, sodium lauroyl sarcosinate is present in an amount of from 0.6% to 0.9% by weight of the composition and the betaine is present in an amount of from 1.1% to 1.4% by weight of the composition. In some embodiments, sodium lauroyl sarcosinate is present in an amount of from 0.7% to 0.9% by weight of the composition and the betaine is present in an amount of from 1.1% to 1.3% by weight of the composition. In some embodiments, sodium lauroyl sarcosinate is present in an amount of from 0.75% to 0.85% by weight of the composition and the betaine is present in an amount of from 1.15% to 1.25% by weight of the composition. In some embodiments, sodium lauroyl sarcosinate is present in an amount of about 0.8% by weight of the composition and the betaine is present in an amount of about 1.2% by weight of the composition.

In some embodiments, the weight ratio of sodium lauroyl sarcosinate to the betaine is from 1:1.2 to 1:3, e.g., from 1:1.2 to 1:2.5, from 1:1.2 to 1:2, from 1:1.2 to 1:1.8, from 1:1.2 to 1:1.7, from 1:1.2 to 1:1.6, from 1:1.3 to 1:3, from 1:1.3 to 1:2.5, from 1:1.3 to 1:2, from 1:1.3 to 1:1.8, from 1:1.3 to 1:1.7, from 1:1.3 to 1:1.6, from 1:1.4 to 1:3, from 1:1.4 to 1:2.5, from 1:1.4 to 1:2, from 1:1.4 to 1:1.8, from 1:1.4 to 1:1.7, from 1:1.4 to 1:1.6, or about 1:1.5.

In another aspect, the invention provides a method comprising applying an effective amount of an oral care composition as disclosed herein to the oral cavity of a subject in need thereof, e.g., by brushing, to (i) reduce or inhibit formation of dental caries, (ii) reduce, repair or inhibit pre-carious lesions of the enamel, (iii) reduce or inhibit demineralization and promote remineralization of the teeth, (iv) reduce hypersensitivity of the teeth, (v) reduce or inhibit gingivitis, (vi) promote healing of sores or cuts in the oral cavity, (vii) reduce levels of acid producing bacteria, (viii) reduce or inhibit microbial biofilm formation in the oral cavity, (ix) reduce or inhibit plaque formation in the oral cavity, (x) promote systemic health, or (xi) clean teeth and oral cavity.

In another aspect, the invention provides the use of sodium lauroyl sarcosinate and a betaine in an oral care composition, e.g., toothpaste or gel, which is free of sodium lauryl sulfate (SLS) for improve foaming properties of the composition, e.g., increasing foam production, wherein the weight ratio of sodium lauroyl sarcosinate to the betaine is from 1:1.1 to 1:3.5. In some embodiments, the betaine is cocamidopropyl betaine.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

DETAILED DESCRIPTION

The following description of various typical aspect(s) is merely exemplary in nature and is in no way intended to limit the disclosure, its application, or uses.

As used throughout, ranges are used as shorthand for describing each and every value that is within the range. Any value within the range can be selected as the terminus of the range.

Unless otherwise specified, all percentages and amounts expressed herein and elsewhere in the specification should be understood to refer to percentages by weight. The amounts given are based on the active weight of the material.

A good substitute for SLS should meet three requirements. First, it should have as good foam ability as SLS since foam performance is important to consumers for a cleansing sensation. Second, it should cause low or even no irritation to oral mucosa. Third, the substitute should be cost effective. Considering all the requirements, sodium lauroyl sarcosinate together with a betaine has been explored in the present invention. It has been found that an optimal combination of sodium lauroyl sarcosinate at 0.8% and a betaine at 1.2% in formula exhibits excellent foam performance. Thus, the combination of sodium lauroyl sarcosinate and a betaine at certain amounts as disclosed herein can replace SLS to achieve better foaming property and lower irritation.

The present invention provides, in an aspect, an oral care composition (Compositions 1.0), e.g., toothpaste or gel, comprising sodium lauroyl sarcosinate and a betaine, wherein the weight ratio of sodium lauroyl sarcosinate to the betaine is from 1:1.1 to 1:3.5.

For example, the invention includes:
1.1. Composition 1.0, wherein the betaine is cocamidopropyl betaine.
1.2. Composition 1.0 or 1.1, wherein the weight ratio of sodium lauroyl sarcosinate to the betaine is from 1:1.2 to 1:3, e.g., from 1:1.2 to 1:2.5, from 1:1.2 to 1:2, from 1:1.2 to 1:1.8, from 1:1.2 to 1:1.7, or from 1:1.2 to 1:1.6.

1.3. Any of the preceding compositions, wherein the weight ratio of sodium lauroyl sarcosinate to the betaine is from 1:1.3 to 1:3, e.g., from 1:1.3 to 1:2.5, from 1:1.3 to 1:2, from 1:1.3 to 1:1.8, from 1:1.3 to 1:1.7, or from 1:1.3 to 1:1.6.

1.4. Any of the preceding compositions, wherein the weight ratio of sodium lauroyl sarcosinate to the betaine is from 1:1.4 to 1:3, e.g., from 1:1.4 to 1:2.5, from 1:1.4 to 1:2, from 1:1.4 to 1:1.8, or from 1:1.4 to 1:1.7.

1.5. Any of the preceding compositions, wherein the weight ratio of sodium lauroyl sarcosinate to the betaine is from 1:1.4 to 1:1.6, e.g., about 1:1.5.

1.6. Any of the preceding compositions, wherein sodium lauroyl sarcosinate is present in an amount of from 0.5% to 1% by weight of the composition and the betaine is present in an amount of from 1% to 1.5% by weight of the composition.

1.7. Any of the preceding compositions, wherein sodium lauroyl sarcosinate is present in an amount of from 0.5% to 0.9% by weight of the composition and the betaine is present in an amount of from 1.1% to 1.5% by weight of the composition.

1.8. Any of the preceding compositions, wherein sodium lauroyl sarcosinate is present in an amount of from 0.6% to 0.9% by weight of the composition and the betaine is present in an amount of from 1.1% to 1.4% by weight of the composition.

1.9. Any of the preceding compositions, wherein sodium lauroyl sarcosinate is present in an amount of from 0.7% to 0.9% by weight of the composition and the betaine is present in an amount of from 1.1% to 1.3% by weight of the composition.

1.10. Any of the preceding compositions, wherein sodium lauroyl sarcosinate is present in an amount of from 0.75% to 0.85% by weight of the composition and the betaine is present in an amount of from 1.15% to 1.25% by weight of the composition.

1.11. Any of the preceding compositions, wherein sodium lauroyl sarcosinate is present in an amount of about 0.8% by weight of the composition and the betaine is present in an amount of about 1.2% by weight of the composition.

1.12. Any of the preceding compositions, wherein the composition comprises an effective amount of a fluoride ion source, e.g., providing 500 to 3000 ppm fluoride.

1.13. Any of the preceding compositions, wherein the fluoride ion source is a salt selected from stannous fluoride, sodium fluoride, potassium fluoride, sodium monofluorophosphate, sodium fluorosilicate, ammonium fluorosilicate, amine fluoride (e.g., olaflur (N'-octadecyltrimethylenediamine-N,N,N'-tris(2-ethanol)-dihydrofluoride)), ammonium fluoride, titanium fluoride, hexafluorosulfate, and combinations thereof, optionally wherein the fluoride ion source is sodium fluoride or sodium monofluorophosphate.

1.14. Any of the preceding compositions, wherein the fluoride ion source is sodium fluoride.

1.15. Any of the preceding compositions, wherein the composition comprises a basic amino acid.

1.16. Any of the preceding compositions, wherein the basic amino acid comprises one or more of arginine, lysine, citrulline, ornithine, creatine, histidine, diaminobutyric acid, diaminopropionic acid, salts thereof, or combinations thereof.

1.17. Any of the preceding compositions, wherein the basic amino acid has the L-configuration.

1.18. Any of the preceding compositions, wherein the basic amino acid is present in an amount of from 1% to 15%, e.g., from 1% to 10%, from 3% to 10%, from 4% to 8%, from 5% to 7%, from 4% to 12%, from 4% to 10%, from 6% to 10%, about 8%, or about 6% by weight of the composition, being calculated as free base form.

1.19. Any of the preceding compositions, wherein the basic amino acid comprises arginine.

1.20. Any of the preceding compositions, wherein the basic amino acid comprises L-arginine.

1.21. Any of the preceding compositions, wherein the basic amino acid comprises arginine bicarbonate, arginine phosphate, arginine sulfate, arginine hydrochloride or combinations thereof, optionally wherein the basic amino acid is arginine bicarbonate.

1.22. Any of the preceding compositions, wherein the composition comprises an abrasive.

1.23. Any of the preceding compositions, wherein the abrasive is selected from silica abrasives, calcium phosphate abrasives, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal) or calcium pyrophosphate; calcium carbonate abrasive; or abrasives such as sodium metaphosphate, potassium metaphosphate, aluminum silicate, calcined alumina, bentonite or other siliceous materials, and combinations thereof.

1.24. Any of the preceding compositions, wherein the abrasive is present in an amount of from 10% to 70%, e.g., from 10% to 30%, e.g., 10% to 20%, 15% to 25%, from 20% to 50%, from 25% to 45%, or from 30% to 40% by weight of the composition.

1.25. Any of the preceding compositions, wherein the abrasive comprises a silica abrasive.

1.26. Any of the preceding compositions, wherein the silica abrasive is present in an amount of from 10% to 30%, e.g., 10% to 20%, 15% to 25%, or about 16%, by weight of the composition.

1.27. Any of the preceding compositions, wherein the abrasive comprises a calcium-containing abrasive, optionally wherein the calcium-containing abrasive is selected from calcium carbonate, calcium phosphate (e.g., dicalcium phosphate dihydrate), calcium sulfate, and combinations thereof.

1.28. Any of the preceding compositions, wherein the abrasive comprises calcium carbonate, optionally wherein the calcium carbonate comprises precipitated calcium carbonate.

1.29. Any of the preceding compositions, wherein the abrasive comprises calcium phosphate (e.g., dicalcium phosphate dihydrate).

1.30. Any of the preceding compositions, wherein the composition comprises one or more soluble phosphate salts, e.g., selected from tetrasodium pyrophosphate (TSPP), sodium tripolyphosphate (STPP) and combinations thereof.

1.31. Any of the preceding compositions, wherein the composition comprises a zinc ion source.

1.32. Any of the preceding compositions, wherein the zinc ion source is selected from the group consisting of zinc oxide, zinc sulfate, zinc chloride, zinc citrate, zinc lactate, zinc gluconate, zinc malate, zinc tartrate, zinc carbonate, zinc phosphate and a combination thereof.

1.33. Any of the preceding compositions, wherein the zinc ion source is selected from the group consisting of zinc oxide, zinc citrate, and a combination thereof.

1.34. Any of the preceding compositions, wherein the zinc ion source is present an amount of from 0.01% to 5%, e.g., 0.1% to 4%, or 0.5% to 3%, by weight of the composition.

1.35. Any of the preceding compositions, wherein the composition comprises a humectant.

1.36. Any of the preceding compositions, wherein the humectant comprises glycerin or sorbitol, optionally wherein glycerin or sorbitol is present in an amount of from 10% to 60%, from 20% to 50%, from 20% to 40%, from 40% to 50%, or from 30% to 40% by weight of the composition.

1.37. Any of the preceding compositions, wherein the composition comprises a thickener.

1.38. Any of the preceding compositions, wherein the thickener comprises carboxymethyl cellulose, optionally wherein carboxymethyl cellulose is present in an amount of from 0.4% to 2%, from 0.8% to 1.5%, from 1% to 1.3%, from 1% to 1.2%, from 0.4% to 0.6%, or about 0.5% by weight of the composition.

1.39. Any of the preceding compositions, wherein the thickener comprises a thickening silica, optionally wherein the thickening silica is present in an amount of from 5 to 10%, from 6% to 8% or about 7%, by weight of the composition, further optionally wherein the thickening silica is present in an amount of from 6% to 8% by weight of the composition.

1.40. Any of the preceding compositions, wherein the composition is free of sodium lauryl sulfate.

1.41. Any of the preceding compositions, wherein the composition does not contain any additional surfactant other than sodium lauroyl sarcosinate and the betaine.

1.42. Any of the preceding compositions, wherein the composition is a toothpaste or gel.

1.43. Any of the preceding compositions, wherein the composition is a toothpaste.

The surfactant system of the invention comprises sodium lauroyl sarcosinate and a betaine. In some embodiments, the surfactant system is free of sodium lauryl sulfate (SLS). In some embodiments, the surfactant system consists of sodium lauroyl sarcosinate and a betaine. The weight ratio of sodium lauroyl sarcosinate to the betaine is from 1:1.1 to 1:3.5. In some embodiments, the betaine is cocamidopropyl betaine (CAPB).

The amount of surfactants, e.g., sodium lauroyl sarcosinate and betaine, disclosed in this disclosure refers to the amount of surfactant present in the composition but not the amount of surfactant solution added into the composition. For example, the amount of CAPB present in a composition containing 3.33% CAPB solution (30%) is regarded to be about 1% by weight of the composition in this disclosure.

In some embodiments, sodium lauroyl sarcosinate is present in an amount of from 0.5% to 1% by weight of the composition and the betaine is present in an amount of from 1% to 1.5% by weight of the composition. In some embodiments, sodium lauroyl sarcosinate is present in an amount of from 0.5% to 0.9% by weight of the composition and betaine is present in an amount of from 1.1% to 1.5% by weight of the composition. In some embodiments, sodium lauroyl sarcosinate is present in an amount of from 0.6% to 0.9% by weight of the composition and the betaine is present in an amount of from 1.1% to 1.4% by weight of the composition. In some embodiments, sodium lauroyl sarcosinate is present in an amount of from 0.7% to 0.9% by weight of the composition and the betaine is present in an amount of from 1.1% to 1.3% by weight of the composition. In some embodiments, sodium lauroyl sarcosinate is present in an amount of from 0.75% to 0.85% by weight of the composition and the betaine is present in an amount of from 1.15% to 1.25% by weight of the composition. In some embodiments, sodium lauroyl sarcosinate is present in an amount of about 0.8% by weight of the composition and the betaine is present in an amount of about 1.2% by weight of the composition.

In some embodiments, the weight ratio of sodium lauroyl sarcosinate to the betaine is from 1:1.2 to 1:3, e.g., from 1:1.2 to 1:2.5, from 1:1.2 to 1:2, from 1:1.2 to 1:1.8, from 1:1.2 to 1:1.7, from 1:1.2 to 1:1.6, from 1:1.3 to 1:3, from 1:1.3 to 1:2.5, from 1:1.3 to 1:2, from 1:1.3 to 1:1.8, from 1:1.3 to 1:1.7, from 1:1.3 to 1:1.6, from 1:1.4 to 1:3, from 1:1.4 to 1:2.5, from 1:1.4 to 1:2, from 1:1.4 to 1:1.8, from 1:1.4 to 1:1.7, from 1:1.4 to 1:1.6, or about 1:1.5.

The oral care composition of the invention can be in the form of any oral care formulations, including dentifrice, toothpaste, gel, powder, cream, strip, gum, bead, film, floss or any other known in the art. In some embodiments, the oral care composition is a toothpaste or gel. In some embodiments, the oral care composition is a toothpaste.

The oral care composition of the invention may be a single phase oral care composition. For example, all the components of the oral care composition may be maintained together with one another in a single phase and/or vessel. For example, all the components of the oral care composition may be maintained in a single phase, such as a single homogenous phase. In another embodiment, the oral care composition may be a multi-phase oral care composition.

The oral care composition of the invention may contain an orally acceptable carrier. As used herein, an "orally acceptable carrier" refers to a material or combination of materials that are safe for use in the compositions of the invention, commensurate with a reasonable benefit/risk ratio. Such materials include but are not limited to, for example, water, humectants, ionic active ingredients, buffering agents, anti-calculus agents, abrasive polishing materials, peroxide sources, alkali metal bicarbonate salts, surfactants, titanium dioxide, coloring agents, flavor systems, sweetening agents, antimicrobial agents, herbal agents, desensitizing agents, stain reducing agents, and mixtures thereof. Such materials are well known in the art and are readily chosen by one skilled in the art based on the physical and aesthetic properties desired for the compositions being prepared. In some embodiment, the orally acceptable carrier may include an orally acceptable solvent. Illustrative solvents may include, but are not limited to, one or more of ethanol, phenoxyethanol, isopropanol, water, cyclohexane, methyl glycol acetate, benzyl alcohol, or the like, or any mixture or combination thereof. In a particular embodiment, the orally acceptable solvent includes benzyl alcohol.

Water may be present in the oral compositions of the invention. Water employed in the preparation of commercial oral compositions should be deionized and free of organic impurities. Water commonly makes up the balance of the compositions and includes about 10% to about 80%, about 20% to about 60%, about 20% to 50%, about 20% to 40%, about 10% to about 30%, about 20% to 30%, about 30% to about 50%, about 30% to about 45%, about 30% to about 40%, or about 25% to 35% by weight of the oral compositions. This amount of water includes the free water which is added plus that amount which is introduced with other materials such as with sorbitol or any components of the invention.

The oral care composition of the invention includes one or more abrasives or an abrasive system including one or more abrasives. The abrasives, e.g., silica abrasives, may be present in an amount of from 10% to 30%, e.g., from 15% to 30%, e.g., from 15% to 25%, from 15% to 20%, from 20% to 30%, or from 20% to 25% by weight of the composition. As used herein, the term "abrasive" may also refer to materials commonly referred to as "polishing agents". Any orally acceptable abrasive may be used, but preferably, type, fineness (particle size), and amount of the abrasive may be selected such that the tooth enamel is not excessively abraded in normal use of the oral care composition. The one or more abrasives may have a particle size or D50 of less than or equal to about 10 μm, less than or equal to about 8 μm, less than or equal to about 5 μm, or less than or equal to about 3 μm. The one or more abrasives may have a particle size or D50 of greater than or equal to about 0.01 μm, greater than or equal to about 0.05 μm, greater than or equal to about 0.1 μm, greater than or equal to about 0.5 μm, or greater than or equal to about 1 μm. Illustrative abrasives may include, but are not limited to, metaphosphate compounds, phosphate salts (e.g., insoluble phosphate salts), such as sodium metaphosphate, potassium metaphosphate, calcium pyrophosphate, magnesium orthophosphate, trimagnesium orthophosphate, tricalcium phosphate, dicalcium phosphate dihydrate, anhydrous dicalcium phosphate, calcium carbonate (e.g., precipitated calcium carbonate and/or natural calcium carbonate), magnesium carbonate, hydrated alumina, silica, zirconium silicate, aluminum silicate including calcined aluminum silicate, polymethyl methacrylate, or the like, or mixtures and combinations thereof.

In some embodiments, the oral care composition comprises a silica abrasive. In some embodiments, the oral care composition comprises a calcium-free silica abrasive.

In some embodiments, the oral care composition of the invention comprises a calcium-containing abrasive (e.g., calcium carbonate). In some embodiments, the calcium-containing abrasive is selected from calcium carbonate, calcium phosphate (e.g., dicalcium phosphate dihydrate), calcium sulfate, and combinations thereof. In some embodiments, the oral care composition comprises calcium carbonate as an abrasive. In one embodiment, the oral care composition comprises precipitated calcium carbonate or natural calcium carbonate. Precipitated calcium carbonate may be preferred over natural calcium carbonate.

In some embodiments, the oral care composition may include fluoride, such as one or more fluoride ion sources (e.g., soluble fluoride salts). A wide variety of fluoride ion-yielding materials may be employed as sources of soluble fluoride. Illustrative fluoride ion sources include, but are not limited to, sodium fluoride, stannous fluoride, potassium fluoride, sodium monofluorophosphate, fluorosilicate salts, such as sodium fluorosilicate and ammonium fluorosilicate, amine fluoride, ammonium fluoride, and combinations thereof. In some embodiments, the fluoride ion source is an amine fluoride (e.g., olaflur (N'-octadecyltrimethylenediamine-N,N,N'-tris(2-ethanol)-dihydrofluoride)) or amine base plus fluoride. In some embodiment, the fluoride ion source is sodium fluoride. The fluoride ion sources may be present in an amount sufficient to supply 25 ppm to 5,000 ppm of fluoride ions, generally, at least 500 ppm, e.g., 500 to 2000 ppm, e.g., 1000 ppm to 1600 ppm, e.g., 1450 ppm.

In some embodiments, the oral care composition of the invention comprises a basic amino acid in free or salt form. The basic amino acids which can be used in the compositions include not only naturally occurring basic amino acids, such as arginine, lysine, and histidine, but also any basic amino acids having a carboxyl group and an amino group in the molecule, which are water-soluble and provide an aqueous solution with a pH of about 7 or greater. Accordingly, basic amino acids include, but are not limited to, arginine, lysine, citrulline, ornithine, creatine, histidine, diaminobutyric acid, diaminopropionic acid, salts thereof or combinations thereof. In a particular embodiment, the basic amino acids are selected from arginine, lysine, citrulline, and ornithine. The basic amino acids of the oral care composition may generally be present in the L-form or L-configuration. The basic amino acids may be provided as a salt of a di- or tri-peptide including the amino acid. In some embodiments, at least a portion of the basic amino acid present in the oral care composition is in the salt form. In some embodiments, the basic amino acid is arginine, for example, L-arginine, or a salt thereof. Arginine may be provided as free arginine or a salt thereof. For example, Arginine may be provided as arginine phosphate, arginine hydrochloride, arginine sulfate, arginine bicarbonate, or the like, and mixtures or combinations thereof. The basic amino acid may be provided as a solution or a solid. For example, the basic amino acid may be provided as an aqueous solution. In some embodiment, the amino acid includes or is provided by an arginine bicarbonate solution. For example, the amino acid may be provided by an about 40% solution of the basic amino acid, such as arginine bicarbonate or alternatively called as arginine carbamate. In some embodiments, the basic amino acid is present in an amount of from 1% to 15%, e.g., from 1% to 10%, from 1% to 5%, from 1% to 3%, from 1% to 2%, from 1.2% to 1.8%, from 1.4% to 1.6%, or about 1.5% by weight of the composition, being calculated as free base form.

In some embodiments, the oral care composition of the invention comprises a zinc ion source. The zinc ion source may be or include a zinc ion and/or one or more zinc salts. For example, the zinc salts may at least partially dissociate in an aqueous solution to produce zinc ions. Illustrative zinc salts may include, but are not limited to, zinc lactate, zinc oxide, zinc chloride, zinc phosphate, zinc citrate, zinc acetate, zinc borate, zinc butyrate, zinc carbonate, zinc formate, zinc gluconate, zinc glycerate, zinc glycolate, zinc picolinate, zinc propionate, zinc salicylate, zinc silicate, zinc stearate, zinc tartrate, zinc undecylenate, and mixtures thereof. In some embodiments, the zinc ion source is present in an amount of from 0.01% to 5%, e.g., 0.1% to 4%, or 1% to 3%, by weight of the composition.

In some embodiments, the zinc ion source is selected from zinc oxide, zinc citrate, and a combination thereof. Zinc oxide may be present in an amount of 0.5% to 2%, e.g., 0.5% to 1.5%, or about 1% by weight of the composition. Zinc citrate may be present in an amount of 0.1% to 1%, 0.25% to 0.75%, about 0.5% by weight of the composition by weight of the composition. In some embodiments, the composition comprises zinc oxide and zinc citrate. The composition may comprise zinc oxide in an amount of 0.5% to 2%, e.g., 0.5% to 1.5%, about 1% or about 1.2% by weight of the composition and zinc citrate in an amount of 0.1% to 1%, 0.25% to 0.75%, about 0.5% by weight of the composition. In certain embodiments, the composition comprises zinc oxide in an amount of about 1% by weight of the composition and zinc citrate in an amount of about 0.5% by weight of the composition.

The oral care composition of the invention may include thickeners. Suitable thickeners may be any orally acceptable thickener or thickening agent configured to control the viscosity of the oral care composition. Illustrative thickeners may be or include, but are not limited to, colloidal silica, fumed silica, a cross-linked polyvinylpyrrolidone (PVP) polymer, cross-linked polyvinylpyrrolidone (PVP), or the like, or mixtures or combinations thereof. In some embodiments, the thickening system includes a cross-linked polyvinylpyrrolidone (PVP) polymer. The thickening system may also include POLYPLASDONE® XL 10F, which is commercially available from Ashland Inc. of Covington, Ky. Illustrative thickeners may also be or include, but are not limited to, carbomers (e.g., carboxyvinyl polymers), carrageenans (e.g., Irish moss, carrageenan, iota-carrageenan, etc.), high molecular weight polyethylene glycols (e.g., CARBOWAX®, which is commercially available from The Dow Chemical Company of Midland, Mich.), cellulosic polymers, hydroxyethylcellulose, carboxymethylcellulose, and salts thereof (e.g., CMC sodium), natural gums (e.g., karaya, xanthan, gum arabic, and tragacanth), colloidal magnesium aluminum silicate, or the like, or mixtures or combinations thereof. Thickeners particularly suitable of use in the oral care composition of the invention include natural and synthetic gums and colloids. In some embodiments, the composition comprises at least one gum selected from carrageenan and xanthan gum. In some embodiments, the composition comprises carboxymethyl cellulose. Carboxymethyl cellulose may be present in an amount of from 0.4% to 2%, from 0.8% to 1.5%, from 1% to 1.3%, from 1% to 1.2%, from 0.4% to 0.6%, or about 0.5% by weight of the composition.

In some embodiments, the oral care compositions of the invention may include one or more humectants. Humectants can reduce evaporation and also contribute towards preservation by lowering water activity and can also impart desirable sweetness or flavor to compositions. Illustrative humectants may be or include, but are not limited to, glycerin, propylene glycol, polyethylene glycol, sorbitol, xylitol, or the like, or any mixture or combination thereof. In some embodiments, the humectant comprises glycerin, sorbitol or a combination thereof. In some embodiments, the humectant may be present in an amount of from 10% to 60%, from 20% to 50%, from 20% to 40%, from 40% to 50%, or from 30% to 40% by weight of the composition.

The oral care composition of the invention may include a preservative. Suitable preservatives include, but are not limited to, sodium benzoate, potassium sorbate, methylisothiazolinone, paraben preservatives, for example methyl p-hydroxybenzoate, propyl p-hydroxybenzoate, and mixtures thereof.

The oral care composition of the invention may include a sweetener such as, for example, saccharin, for example sodium saccharin, acesulfam, neotame, cyclamate or sucralose; natural high-intensity sweeteners such as thaumatin, stevioside or glycyrrhizin; or such as sorbitol, xylitol, maltitol or mannitol. One or more of such sweeteners may be present in an amount of from 0.005% to 5% by weight, for example 0.01% to 1%, for example 0.01% to 0.5%, by weight of the composition.

The oral care composition of the invention may include a flavoring agent. Suitable flavoring agents include, but are not limited to, essential oils and various flavoring aldehydes, esters, alcohols, and similar materials, as well as sweeteners such as sodium saccharin. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. The flavoring agent is typically incorporated in the oral composition at a concentration of 0.01 to 3% by weight.

The oral care composition of the invention may include one or more pH modifying agents. For example, the oral care composition may include one or more acidifying agents and/or one or more basifying agents configured to reduce and/or increase the pH thereof, respectively. Illustrative acidifying agents and/or one or more basifying agents may be or include, but are not limited to, an alkali metal hydroxide, such as sodium hydroxide and/or potassium hydroxide, citric acid, hydrochloric acid, or the like, or combinations thereof.

The oral care composition of the invention may also include one or more buffering agents configured to control or modulate the pH within a predetermined or desired range. Illustrative buffering agents may include, but are not limited to, sodium bicarbonate, sodium phosphate, sodium carbonate, sodium acid pyrophosphate, sodium citrate, and mixtures thereof. Sodium phosphate may include monosodium phosphate ($NaH_2PO_4$), disodium phosphate ($Na_2HPO_4$), trisodium phosphate ($Na_3PO_4$), and mixtures thereof. In a typical embodiment, the buffering agent may be anhydrous sodium phosphate dibasic or disodium phosphate and/or sodium phosphate monobasic. In another embodiment, the buffering agent includes anhydrous sodium phosphate dibasic or disodium phosphate, and phosphoric acid (e.g., syrupy phosphoric acid; 85%-Food Grade).

The oral care composition of the invention may include anticalculus agents. Illustrative anticalculus agents may include, but are not limited to, phosphates and polyphosphates (e.g., pyrophosphates), polyaminopropanesulfonic acid (AMPS), hexametaphosphate salts, zinc citrate trihydrate, polypeptides, polyolefin sulfonates, polyolefin phosphates, diphosphonates. In some embodiments, the anticalculus agent includes tetrasodium pyrophosphate (TSPP), sodium tripolyphosphate (STPP), or a combination thereof.

The oral care composition of the invention may include an antioxidant. Any orally acceptable antioxidant may be used, including, but not limited to, butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, or the like, or combinations and mixtures thereof.

The oral care composition of the invention may include one or more pigments, such as whitening pigments. In some embodiments, the whitening pigments include particles ranging in size from about 0.1 μm to about 10 μm with a refractive index greater than about 1.2. Suitable whitening agents include, without limitation, titanium dioxide particles, zinc oxide particles, aluminum oxide particles, tin oxide particles, calcium oxide particles, magnesium oxide particles, barium oxide particles, silica particles, zirconium silicate particles, mica particles, talc particles, tetracalcium phosphate particles, amorphous calcium phosphate particles, alpha-tricalcium phosphate particles, beta-tricalcium phosphate particles, hydroxyapatite particles, calcium carbonate particles, zinc phosphate particles, silicon dioxide particles, zirconium silicate particles, or the like, or mixtures and combinations thereof. The whitening pigment, such as titanium dioxide particles, may be present in an amount that is sufficient to whiten the toothpaste.

All ingredients for use in the compositions described herein should be orally acceptable. As used herein, "orally acceptable" may refer any ingredient that is present in a composition as described in an amount and form which does not render the composition unsafe for use in the oral cavity.

In another aspect, the present invention provides a method to (i) reduce or inhibit formation of dental caries, (ii) reduce, repair or inhibit pre-carious lesions of the enamel, (iii) reduce or inhibit demineralization and promote remineralization of the teeth, (iv) reduce hypersensitivity of the teeth, (v) reduce or inhibit gingivitis, (vi) promote healing of sores or cuts in the oral cavity, (vii) reduce levels of acid producing bacteria, (viii) reduce or inhibit microbial biofilm formation in the oral cavity, (ix) reduce or inhibit plaque formation in the oral cavity, (x) promote systemic health, or (xi) clean teeth and oral cavity, comprising applying an effective amount of any of oral care compositions as disclosed herein, e.g., any of Compositions 1 et seq., to the oral cavity of a subject in need thereof. The method may include contacting the oral care composition with water. The method may also include contacting the surface of the teeth with the oral care composition. Contacting the surface of the teeth with the oral care composition may include disposing the oral care composition (e.g., toothpaste) on a toothbrush and brushing the teeth with the toothbrush. The oral care composition may be applied and/or contacted with the surfaces of the teeth at predetermined intervals. For example, a daily basis, at least once a day, twice a day, or more, for multiple days, or alternatively every other day. In another example, the oral care composition may be applied and/or contacted with the surfaces of the teeth at least once a day, at least once every two days, at least once every three days, at least once every five days, at least once a week, at least once every two weeks, or at least once a month. The oral care composition thereof may be utilized for up to 2 weeks, up to 3 weeks, up to 4 weeks, up to 6 weeks, up to 8 weeks, or greater.

In another aspect, the invention provides the use of any of oral care compositions as disclosed herein, e.g., any of Compositions 1 et seq., to (i) reduce or inhibit formation of dental caries, (ii) reduce, repair or inhibit pre-carious lesions of the enamel, (iii) reduce or inhibit demineralization and promote remineralization of the teeth, (iv) reduce hypersensitivity of the teeth, (v) reduce or inhibit gingivitis, (vi) promote healing of sores or cuts in the oral cavity, (vii) reduce levels of acid producing bacteria, (viii) reduce or inhibit microbial biofilm formation in the oral cavity, (ix) reduce or inhibit plaque formation in the oral cavity, (x) promote systemic health, or (xi) clean teeth and oral cavity, in a subject in need thereof.

In another aspect, the invention provides the use of sodium lauroyl sarcosinate and a betaine in an oral care composition, e.g., toothpaste or gel, which is free of sodium lauryl sulfate (SLS), any of oral care compositions as disclosed herein, e.g., any of Compositions 1 et seq., for improving foaming properties of the composition, e.g., increasing foam production, wherein the weight ratio of sodium lauroyl sarcosinate to the betaine is from 1:1.1 to 1:3.5. In some embodiments, the betaine is cocamidopropyl betaine.

In some embodiments, sodium lauroyl sarcosinate is present in an amount of from 0.5% to 1% by weight of the composition and the betaine is present in an amount of from 1% to 1.5% by weight of the composition. In some embodiments, sodium lauroyl sarcosinate is present in an amount of from 0.5% to 0.9% by weight of the composition and the betaine is present in an amount of from 1.1% to 1.5% by weight of the composition. In some embodiments, sodium lauroyl sarcosinate is present in an amount of from 0.6% to 0.9% by weight of the composition and the betaine is present in an amount of from 1.1% to 1.4% by weight of the composition. In some embodiments, sodium lauroyl sarcosinate is present in an amount of from 0.7% to 0.9% by weight of the composition and the betaine is present in an amount of from 1.1% to 1.3% by weight of the composition. In some embodiments, sodium lauroyl sarcosinate is present in an amount of from 0.75% to 0.85% by weight of the composition and the betaine is present in an amount of from 1.15% to 1.25% by weight of the composition. In some embodiments, sodium lauroyl sarcosinate is present in an amount of about 0.8% by weight of the composition and the betaine is present in an amount of about 1.2% by weight of the composition.

In some embodiments, the weight ratio of sodium lauroyl sarcosinate to the betaine is from 1:1.2 to 1:3, e.g., from 1:1.2 to 1:2.5, from 1:1.2 to 1:2, from 1:1.2 to 1:1.8, from 1:1.2 to 1:1.7, from 1:1.2 to 1:1.6, from 1:1.3 to 1:3, from 1:1.3 to 1:2.5, from 1:1.3 to 1:2, from 1:1.3 to 1:1.8, from 1:1.3 to 1:1.7, from 1:1.3 to 1:1.6, from 1:1.4 to 1:3, from 1:1.4 to 1:2.5, from 1:1.4 to 1:2, from 1:1.4 to 1:1.8, from 1:1.4 to 1:1.7, from 1:1.4 to 1:1.6, or about 1:1.5.

EXAMPLES

Example 1

The foam volume generated by a SLS-free base formulation was evaluated with various amounts of sodium lauroyl sarcosinate and cocamidopropyl betaine (CAPB) to determine the impact of the levels of sodium lauroyl sarcosinate and cocamidopropyl betaine (CAPB) on foam generation. Different levels of sodium lauroyl sarcosinate and betaine combination are applied to the same base formulation. The total amount of surfactants was maintained the same as 2%. Seven toothpastes having the formulations as indicated in Table 1 were prepared.

TABLE 1

| Ingredient (wt. %) | Comp. 1 | Comp. 2 | Comp. 3 | Comp. 4 | Comp. 5 | Comp. 6 | Comp. 7 |
| --- | --- | --- | --- | --- | --- | --- | --- |
| Water | 10.66 | 10.66 | 10.66 | 10.66 | 10.66 | 10.66 | 10.66 |
| Sorbitol (70% soln.) | 68 | 68 | 68 | 68 | 68 | 68 | 68 |
| Carboxymethyl cellulose | 0.5 | 0.5 | 0.5 | 0.5 | 0.5 | 0.5 | 0.5 |
| Sodium fluoride | 0.22 | 0.22 | 0.22 | 0.22 | 0.22 | 0.22 | 0.22 |
| Silica | 16 | 16 | 16 | 16 | 16 | 16 | 16 |
| PEG 600 | 1 | 1 | 1 | 1 | 1 | 1 | 1 |
| Sodium lauroyl sarcosinate | 0 | 0.4 | 0.8 | 1 | 1.2 | 1.6 | 2 |
| CAPB | 2 | 1.6 | 1.2 | 1 | 0.8 | 0.4 | 0 |
| Flavor, sweetener, film, and colors | Balance | Balance | Balance | Balance | Balance | Balance | Balance |

The foam performance of the toothpastes was evaluated using a foam spin instrument. Foam was generated from a slurry sample of toothpaste and water in a 1:4 ratio in the following condition: 2500 rpm/min, stirring 120 s, 80 ml slurry. Foam volume was measure at 16 second and 120 second. Foam volume measured at 16 second reflects the foam speed of test samples. The higher foam volume at 16 second means the faster they can generate foam. Foam volume measured at 120 second reflects the max foam volume of test samples. The higher foam volume at 120 second means the larger amount of foam they can generate. The results are shown in Table 2. All results are average of 3 replicas.

TABLE 2

| Compositions | Foam Volume (mL) | |
|---|---|---|
| | 16 sec | 120 sec |
| Comp. 1 (2% Betaine) | 2.59 | 92.08 |
| Comp. 2 (0.4% Sodium lauroyl sarcosinate + 1.6% Betaine) | 32.37 | 152.5 |
| Comp. 3 (0.8% Sodium lauroyl sarcosinate + 1.2% Betaine) | 74.38 | 156.24 |
| Comp. 4 (1.0% Sodium lauroyl sarcosinate + 1.0% Betaine) | 57.55 | 147.46 |
| Comp. 5 (1.2% Sodium lauroyl sarcosinate + 0.8% Betaine) | 48.12 | 138.33 |
| Comp. 6 (1.6% Sodium lauroyl sarcosinate + 0.4% Betaine) | 24.31 | 131.5 |
| Comp. 7 (2.0% Sodium lauroyl sarcosinate) | 0 | 106.18 |

As shown in Table 2, Composition 3 containing 0.8% sodium lauroyl sarcosinate and 1.2% betaine exhibited the best foam performance, in terms of both foam speed and max foam volume. It was even better than sodium lauroyl sarcosinate (2% in formula) or betaine (2% in formula) alone.

Example 2

Composition 3, which showed the best foam performance, was compared with two commercially available toothpastes (Compositions C1 and C2). Composition C1 contains 2% SLS as surfactant. Composition C2 contains 2.3% SLS and 0.375% CAPB. The formulation of the tested toothpastes is shown in Table 3.

TABLE 3

| Ingredient (wt. %) | Comp. 3 | Comp. C1 | Comp. C2 |
|---|---|---|---|
| Water | 10.66 | 18.81 | 9.98 |
| Sorbitol (70% soln.) | 68 | 31 | 68 |
| Carboxymethyl cellulose | 0.5 | 0.8 | 0.5 |
| Sodium fluoride | 0.22 | 0.1 | 0.22 |
| Sodium MPF | 0 | 0.76 | 0 |
| Silica | 16 | 0 | 16 |
| Dicalcium phosphate dihydrate | 0 | 45 | 0 |
| PEG 600 | 1 | 0 | 1 |
| Tetrasodium pyrophosphate | 0 | 0.25 | 0 |

TABLE 3-continued

| Ingredient (wt. %) | Comp. 3 | Comp. C1 | Comp. C2 |
|---|---|---|---|
| SLS | 0 | 2 | 2.3 |
| Sodium lauroyl sarcosinate | 0.8 | 0 | 0 |
| CAPB | 1.2 | 0 | 0.375 |
| Flavor, sweetener, film, and colors | Balance | Balance | Balance |

The foam performance of the toothpastes was evaluated using a foam spin instrument as described in Example 1. Bubble size (diameter) was also measured at 30 sec. The results are shown in Table 4. All results are average of 3 replicas.

TABLE 4

| Compositions | Foam Volume (mL) | | Bubble size (mm) |
|---|---|---|---|
| | 16 sec | 120 sec | 30 sec |
| Comp. 3 | 74.38 | 156.24 | 0.196 |
| Comp. C1 (2.0% SLS) | 72.08 | 122.72 | 0.184 |
| Comp. C2 (2.3% SLS + 0.375% Betaine) | 79.99 | 136.53 | 0.207 |

The results in Table 4 shows that the optimal combination of sodium lauroyl sarcosinate and betaine (Composition 3) exhibited the best foaming performance, compared to SLS alone (Composition C1) or the combination of SLS and betaine (Composition C2), in terms of max foam volume. Foam speed and bubble size of the three compositions were comparable. It is worth noting that the optimal combination of 0.8% sodium lauroyl sarcosinate and 1.2% CAPB (Composition 3) exhibited better foaming performance than the combination of 2.3% SLS and 0.375% CAPB (Composition C2), even at lower total surfactant level (2% vs. 2.675%).

The invention claimed is:

1. An oral care composition comprising sodium lauroyl sarcosinate and cocamidopropyl betaine, wherein sodium lauroyl sarcosinate is present in an amount of from 0.6% to 0.9% by weight of the composition and the cocamidopropyl betaine is present in an amount of from 1.1% to 1.4% by weight of the composition; and water; wherein the oral care composition is a toothpaste or gel.

2. The oral care composition of claim 1, wherein the weight ratio of sodium lauroyl sarcosinate to the cocamidopropyl betaine is from 1:1.2 to 1:3.

3. The oral care composition of claim 1, wherein the weight ratio of sodium lauroyl sarcosinate to the cocamidopropyl betaine is from 1:1.4 to 1:1.6.

4. The oral care composition of claim 1, wherein the composition comprises a fluoride ion source.

5. The oral care composition of claim 1, wherein the composition comprises a basic amino acid.

6. The oral care composition of claim 1, wherein the composition comprises a zinc ion source.

7. The oral care composition of claim 1, wherein the composition is free of sodium lauryl sulfate (SLS).

* * * * *